(12) United States Patent
Kleen et al.

(10) Patent No.: US 7,343,036 B2
(45) Date of Patent: Mar. 11, 2008

(54) IMAGING METHOD FOR A CAPSULE-TYPE ENDOSCOPE UNIT

(75) Inventors: Martin Kleen, Neunkirchen (DE); Rainer Kuth, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 682 days.

(21) Appl. No.: 10/829,322

(22) Filed: Apr. 22, 2004

(65) Prior Publication Data

US 2004/0264754 A1    Dec. 30, 2004

(30) Foreign Application Priority Data

Apr. 22, 2003    (DE)    ................. 103 18 205

(51) Int. Cl.
*G06K 9/00*    (2006.01)
(52) U.S. Cl. ................. 382/154; 382/128; 600/424
(58) Field of Classification Search ................. 382/128, 382/129, 130, 131, 132, 133, 107, 154, 162, 382/172, 199, 203, 219, 250, 260, 274, 276, 382/305, 181, 285, 232, 243, 255; 424/1.69; 600/424, 118, 129, 407; 378/20, 21; 356/3.05
See application file for complete search history.

(56) References Cited

U.S. PATENT DOCUMENTS

| | | | |
|---|---|---|---|
| 5,604,531 A | | 2/1997 | Iddan et al. |
| 6,233,476 B1 * | | 5/2001 | Strommer et al. .......... 600/424 |
| 6,918,872 B2 * | | 7/2005 | Yokoi et al. ................ 600/129 |
| 6,928,314 B1 * | | 8/2005 | Johnson et al. ............. 600/407 |
| 6,939,292 B2 * | | 9/2005 | Mizuno ....................... 600/118 |
| 6,944,316 B2 * | | 9/2005 | Glukhovsky et al. ........ 382/107 |
| 7,138,103 B2 * | | 11/2006 | Goldenberg et al. ........ 424/1.69 |

FOREIGN PATENT DOCUMENTS

| | | |
|---|---|---|
| DE | 198 00 765 A1 | 4/1999 |
| JP | 05285087 | 11/1993 |
| WO | WO 01/65995 A2 | 9/2001 |
| WO | WO 02/054932 A2 | 7/2002 |
| WO | WO 02/095351 A2 | 11/2002 |
| WO | WO 03/010967 A1 | 2/2003 |

OTHER PUBLICATIONS

Koichiro Deguchi, et al., "3-D shape Reconstruction from Endoscope Image Sequences by The Factorization Method", IEICE Trans. Inf. & Syst., vol. E79-D, No. 9, Sep. 1996, pp. 1329-1336.

* cited by examiner

*Primary Examiner*—Seyed Azarian
(74) *Attorney, Agent, or Firm*—Harness, Dickey & Pierce, PLC

(57) ABSTRACT

A computer-based 3D imaging method is for a wireless endoscope unit, equipped with a camera, of the size of a capsule that can be swallowed by the patient. A medical apparatus is for the pseudo three-dimensional representation of the surroundings of the endoscope unit. The images recorded by the camera are subjected to a pattern recognition algorithm for identifying common features of chronologically successive individual images. Individual images that show spatially coherent structures are concatenated by superimposing common image features in the course of an image conditioning procedure in order to produce a pseudo three-dimensional representation.

32 Claims, 2 Drawing Sheets

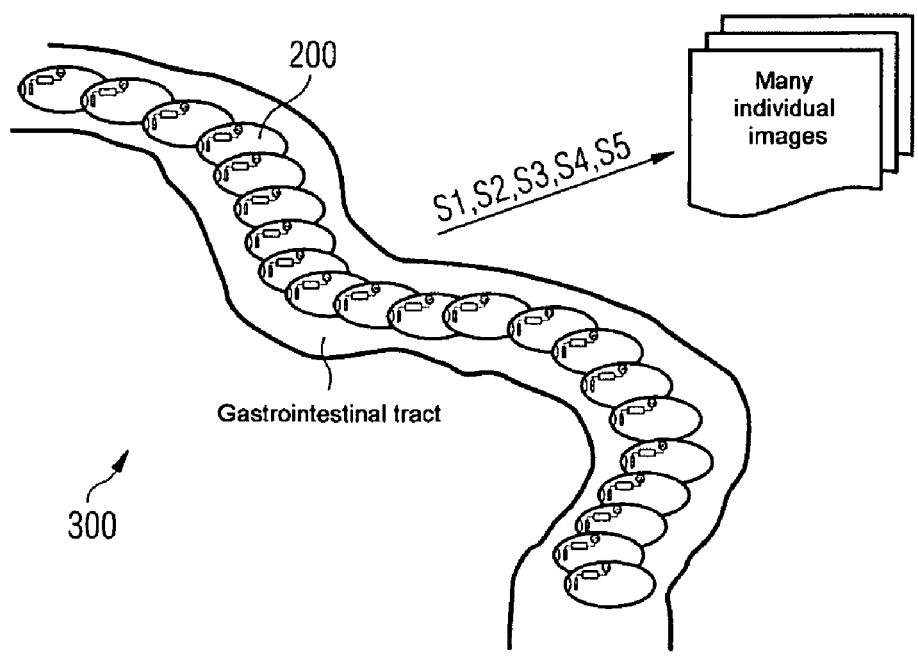
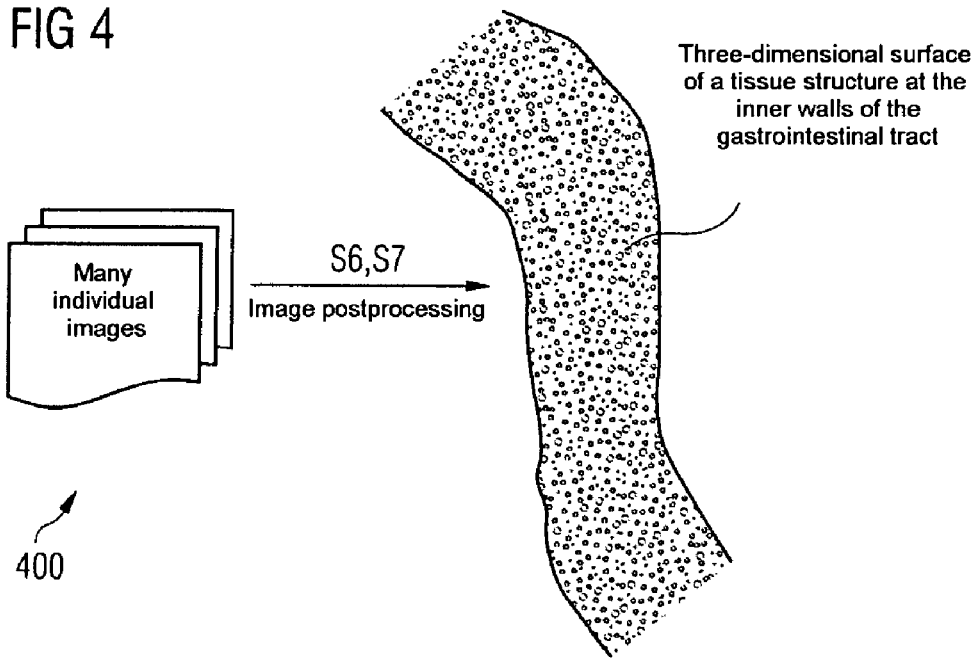

IMAGING METHOD FOR A CAPSULE-TYPE ENDOSCOPE UNIT

The present application hereby claims priority under 35 U.S.C. §119 on German patent application number DE 103 18 205.5 filed Apr. 22, 2003, the entire contents of which are hereby incorporated herein by reference.

FIELD OF THE INVENTION

The invention generally relates to a computer-based 3D imaging method for a wireless endoscope unit. Preferbly, it relates to one equipped with a video camera, of the size of a capsule that can be swallowed by the patient. It further generally relates to a medical apparatus for the three-dimensional representation of body cavities of the patient which can be used, for example, in the field of noninvasive gastroenterological endoscopy.

BACKGROUND OF THE INVENTION

Capsule endoscopy is a new method for diagnosing diseases of the gastrointestinal tract, in particular in the upper sections of the small intestine (jejunum). This permits a patient-friendly, painless investigation of the entire region of the small intestine without physical exposure to radiation. This method of investigation has the advantage that it is possible to inspect areas in which conventional radiological and endoscope methods achieve only inadequate diagnostic results.

In this case, the patient swallows a capsule that is equipped with a miniature color video camera, supplies endoscopic images from the small intestine, and permits painless non-invasive diagnostics. It is also possible to conceive inserting the capsule in the rectum if the aim is solely to carry out a coloscopic examination of the large intestine including the terminal ileum.

The examination begins in this case after fasting and can be carried out on an outpatient basis. After activation and ingestion of the video capsule, the patient can carry on with his customary daily activities without a problem and without noticing the approximately eight-hour passage of the capsule through the gastrointestinal tract. After the capsule has spent on average approximately 80 minutes in the stomach, it requires approximately 90 minutes on average to pass through the small intestine.

Such a capsule endoscope and a diagnostic system for visualizing the entire large intestine mucosa is produced, for exmpel, by the Israeli company Given Imaging Ltd. and marketed under the brand "M2A® Imaging Capsule". The M2A® imaging capsule includes a miniature color video camera, a light source, a miniature transmitter and an antenna. The casing of the capsule is produced from a sealed biocompatible special material that is resistant to digestive secretions in the gastrointestinal tract.

The M2A® imaging capsule is swallowed by the patient and conveyed through the digestive tract because of the peristaltic movement of the gastrointestinal musculature. The size of the video capsule is 11×26 mm, its field of view is about 140°, and it weighs about four grams. It can be used to find lesions with a size of less than 0.1 mm. During a normal (eight-hour) examination process, the capsule produces roughly 57,000 images at a rate of two images per second. The capsule is evacuated in a natural way after having passed the digestive tract.

During its passage through the small intestine, the color video camera takes image sequences that are transmitted in the form of ultrashort waves to a wireless reception unit that is located outside the body, and which the patient carries on a belt around his hips, and are stored in a data recorder after being demodulated and subjected to low-pass filtering and analog-to-digital conversion. The belt, which is comfortable to wear, with the reception unit enables the patient largely to carry on with his customary daily activities during the gastrointestinal examination.

In addition to the image signal, the capsule can also output a locating signal referring to its current position. The point is that it includes metal parts that are located by eight metal detectors applied to the patient's abdominal skin.

It is thereby possible to assign the images to the respective intestinal section. A computer workstation at which the RAPID™ ("Reporting and Processing of Images and Data") software developed by Given Imaging is installed processes the data and compiles a video film of the small intestine as well as relevant additional information relating to the digestive tract. The doctor responsible has the option of viewing this video film in real time, of tracking the position of the M2A® imaging capsule during its passage through the gastrointestinal tract, and of inspecting individual images exactly in freeze mode and processing and archiving them. The gastroenterologist can then locate any pathologies of the small intestine with the aid of the visual information obtained in this way.

In addition to the application of capsule endoscopy in the region of the gastrointestinal tract, numerous further possible applications are currently being planned. This relates generally to the endoscopic examination of cavities in the interior of the body in which the movement of the video capsule is not prevented by the presence of connective tissue. This includes, for example, the endovascular examination of the cerebral blood vessels, the endoscopic examination of the bronchial tract (bronchoscopy) and the minimally invasive endoscopic examination of the abdominal cavity and the abdominal and pelvic viscera (laparoscopy). When the embodiments of the invention are described below with reference to the gastrointestinal tract, it is to be understood that the embodiments of the invention relates in general to the endoscopy of body cavities.

WO 01/065995 A3 presents a system and an associated method for providing images from the interior of the body of a patient who is to be examined. The system includes an imaging system and an RF transmitter of low signal power for transmitting video signals of a CMOS video camera to a reception system that is located outside the body. The imaging system includes at least one CMOS video camera, at least one light source for illuminating a site in the interior of the body, and an optical lens system for focusing the light beams reflected by the site to be examined.

WO 02/054932 A2 discloses a system and a method for wide angle recording of cavities in the internal organs of a patient that are to be examined. The system includes at least one image sensor, light sources and an optical lens system for recording image sequences from the interior of the body. The system can be integrated in a medical unit or fitted on the latter, which is used for introduction into cavities in the interior of the patient's body. This can be, for example, an advancing endoscope, an injection needle, or else a video capsule that can be swallowed by the patient.

The device described in WO 02/095351 A2 relates to a floating, capsule-type image sensor for examining liquid-filled cavities of organs in the interior of a patient's body that has the specific weight of water or some other volume/mass ratio that permits it to float. In an exemplary embodiment of this, the image sensor includes an imaging system that is installed in a floating housing.

A diagnostic unit, system and method for providing images from cavities of organs in the interior of a patient's body, such as the gastrointestinal tract, for example, is disclosed in WO 03/010967 A1. The unit is a floating capsule that contains an image sensor, a microprocessor and a light source for illuminating a cavity in the interior of the body. Moreover, the unit includes an optical system including a number of filters and positive lenses for focusing the light reflected by the cavity walls. The image data recorded by the image sensor are digitized, compressed and transmitted by an integrated RF transmitter to an RF receiver that is located outside the body and is preferably worn on a belt around the patient's abdomen. The image data received are stored in an internal memory chip of the RF receiver. In an exemplary embodiment of the invention, the reception unit can be connected to a workstation that serves to decompress and condition the data stream for the purpose of visualizing the recorded images.

The disadvantage of the capsule endoscopes described above resides in the inaccurate results of inspection, since the video capsule cannot be controlled and passes too quickly through specific regions in the interior of the body, or does not even record them at all. Moreover, uninterrupted transmission of images from the interior of the body is impossible.

OBJECT OF THE PRESENT INVENTION

An embodiment of the present invention includes an object of providing a diagnostic imaging unit and a method for obtaining and processing images with the aid of which it is possible to produce an improved three-dimensional overall representation of body cavities.

An object may be achieved according to an embodiment of the invention. Other exemplary embodiments which develop the idea of the invention in a particularly advantageous way are also specified.

SUMMARY OF THE PRESENT INVENTION

In accordance with an object, an embodiment of the present invention discloses a computer-based medical 3D imaging method for a wireless endoscope unit, equipped with a video camera, in the form of a capsule, as well as a medical apparatus for the three-dimensional representation of, for example, body cavities. The imaging system components used in this case are suitable, for example, for use in the field of non-invasive gastroenterological endoscopy for the diagnosis of symptoms and/or lesions in the region of the human gastrointestinal tract. Moreover, an embodiment of the invention also enables a clinical report to be compiled automatically, as well as enabling digital archiving of findings and image data.

BRIEF DESCRIPTION OF THE DRAWINGS

Further features, advantages and possible applications of the present invention emerge from the following description of preferred exemplary embodiments of the invention, which are depicted in the drawings presented below, and in which:

FIG. 3 shows a sectional illustration of a section of the human gastrointestinal tract during the carrying out of an endoscopic inspection with the aid of a capsule-type endoscope unit, and FIG. 4 shows a diagram illustrating the computer-assisted image processing procedure for producing a three-dimensional representation of the surfaces of tissue structures starting from the image sequence supplied by the capsule-type endoscope unit.

DETAILED DESCRIPTION OF THE EMBODIMENTS

Figure 1:
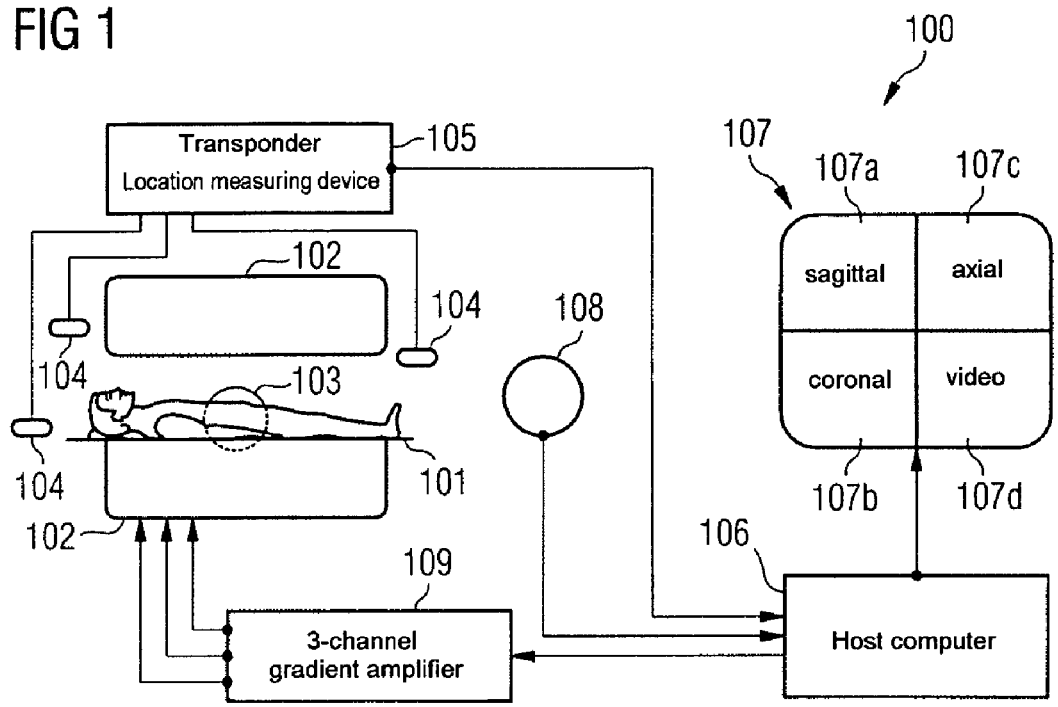
FIG. 1 shows a side view of a medical apparatus for recording and evaluating RF signals from a capsule-type endoscope unit according to an exemplary embodiment of the present invention.
Figure 2:
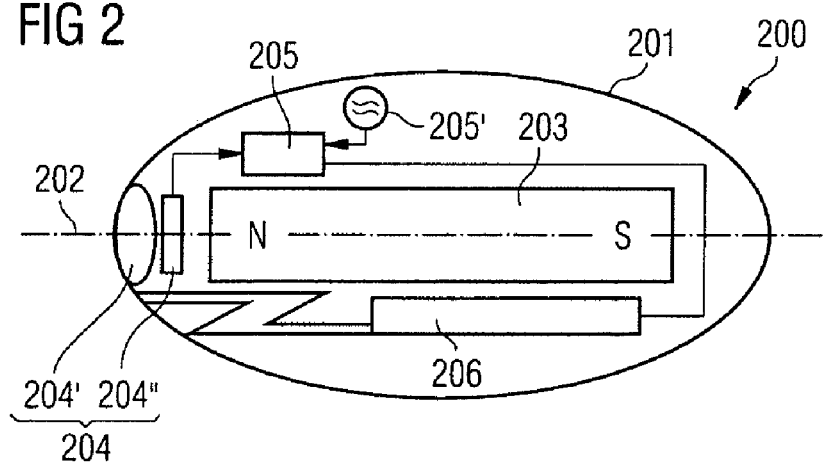
FIG. 2 shows a plan view of the capsule-type endoscope unit used as imaging system component and equipped with a miniature video camera, according to an exemplary embodiment of the present invention.

The first step below is to provide more detail on the inventive imaging method as depicted in FIGS. 3 and 4. Subsequently, the functions of the system components depicted in FIGS. 1 and 2 are explained. The significance of the pictorial elements provided with reference symbols in FIGS. 1 to 4 can be gathered from the attached list of reference symbols.

A first exemplary embodiment of the present invention relates to a computer-assisted 3D imaging method for a wireless, capsule-type endoscope unit 200, equipped with a miniature color video camera 204, for use in, for example, the region of the gastrointestinal tract of a patient. In this case, the capsule is dimensioned in such a way that it can be swallowed by the patient.

The capsules are of correspondingly smaller dimensions when an embodiment of the invention is applied in blood vessels.

The color spectrum of the camera can also in this case cover the infrared and/or ultraviolet spectral region(s). During (passive) transport of the capsule endoscope 200 through the gastrointestinal tract, for example, effected by peristaltic movements of the esophagus, stomach and intestine, the video camera 204 records a sequence of individual images (S1) and transmits (S2) the usually analog image data in the form of electromagnetic RF signals to a reception and evaluation device that is located outside the body and comprises the reception units 103 and 108 and the host computer 106. The received individual images of the analog video stream transmitted by the capsule-type endoscope unit 200 are digitized (S3) there at a frame rate corresponding to the real image update or at a substantially constant image refresh rate (if they have not already been transmitted in digital form) and archived (S4), and can thereafter be displayed graphically (S5).

A pattern recognition algorithm (S6) is executed in this case for identifying substantially corresponding features, that is to say ones which, for example, exceed a prescribed threshold value for the correspondence, of chronologically successive individual images of the recorded image sequence. In order to produce a (pseudo-) three-dimensional representation of the surfaces of tissue structures to be examined, the host computer 106 concatenates individual images, which show spatially coherent structures, by superimposing common image features in the course of an image processing procedure (S7).

The digital image data for the 3D model calculated by the host computer 106 in this way, and which can be represented in a simplified way substantially by a bent tube in the case of the intestine, are then stored in a data memory for later visualization.

According to an embodiment of the invention, in the concatenation of two coherent individual images with the numbers m and n, use is made of the path difference $$\Delta x_{m,n} := x_n - x_m \in IR^3 \text{(in mm)},$$

covered by the capsule-type endoscope unit 200 and loaded with a weighting factor, between the instantaneous recording positions $x_m$ and $x_n$ of the unit for recording the two individual images. These recording positions can be determined in this case either by evaluating X-ray pictures in which the capsule-type endoscope unit 200 can be identified, or by evaluating the signal transit times $T_m$ and $T_n$ of the wireless image data transmission (S2) from the video capsule 200 to the reception units 103 and 108, respectively.

A sectional illustration of a section of the region, recorded by the endoscope unit, which shows the individual phases of the movement of the capsule-type endoscope unit 200, for example through the small intestine of a patient while an endoscopic inspection is being carried out to produce a continuous image sequence, is illustrated in FIG. 3.

FIG. 4 depicts the computer-assisted image conditioning process for producing a (pseudo) three-dimensional representation of the image sequences recorded by the capsule endoscope 200, which show, for example, the surfaces of tissue structures of the mucous membranes on the inner walls of the small intestine.

Together with the image data of each i-th individual image (i in this case being a whole number greater than or equal to one) of the recorded image sequence, according to the invention the, for example, Cartesian space coordinates ($x_i$, $y_i$, $z_i$) of the capsule-type endoscope unit 200 are transmitted, to one of the reception units 103 or 108 for each i-th recording, and archived in a data recorder in digital form.

A further aspect of an embodiment of the present invention relates to a further configuration of this method for automatically compiling (S10) and archiving (S11) a clinical report. A pattern recognition algorithm is carried out for this purpose, and the first step in this is to calculate (S8) the distance squares $$d_{ij}^2 := d^2(x_{Mi}, x_{Rj})$$

for $0 \leq i \leq I-1, 0 \leq j \leq J-1$ between the image parameters, stored in the form of N-dimensional feature vectors $x_{Mi}$, of recorded individual images with the image parameters, stored in the form of N-dimensional reference vectors $x_{Rj}$, of images of diseased tissue structures from a reference image database. This is performed by calculating the square of the Euclidean length $\|\Delta x_{ij}\|_2$ of their difference vectors $\Delta x_{ij}$:

$$d_{ij}^2 := d^2(x_{Mi}, x_{Rj}) = \|\Delta x_{ij}\|_2^2$$
$$= \Delta x_{ij}^T \Delta x_{ij}$$
$$= \sum_{n=0}^{N-1} \Delta x_{ij,n}^2 \forall i, j$$

where $\Delta x_{ij} := x_{Mi} - x_{Rj} \in IR^N$.

Thereafter, the reference vectors $x_{Rj}$ of those reference images are determined (S9) whose distance squares $d_{ij}^2$ are a minimum in relation to the respective feature vectors $x_{Mi}$ of the individual images to be examined. The data of the findings associated with these reference vectors $x_{Rj}$ are then read out from the reference image database.

According to a further aspect of an embodiment of the present invention, the position and the orientation (for example the instantaneous position, the current adjusting angle and/or the path) of the capsule-type endoscope unit 200 are detected in a wireless fashion during the examination and inserted into the (pseudo-) three-dimensional representation, visualized via a display device 107, of the gastrointestinal tract.

After the conclusion of the gastroenterological endoscopy carried out with the aid of the capsule endoscope 200, it is possible, by navigating a cursor in a control window of the operator interface, represented on a display device 107, of a computer program, to produce different camera perspectives for showing different spatial views, for example of tissue structures, in the interior of the gastrointestinal tract by influencing at least two input parameters. These two input parameters are, for example, the magnitude of the advancing movement in the direction of movement of the capsule-type endoscope unit 200, and the magnitude of the rotary movement about an axis pointing in the direction of movement of the capsule endoscope 200.

An embodiment of the invention permits a spatial, temporal and personal decoupling of the operating steps required for image generation in an endoscopy (for example gastroscopy or coloscopy), which is of great importance in practice: a user can view the image sequences independently of the location and time of the inspection process that led to the recording of the images. This has the advantage, inter alia, that redundant inspections of the same sections of the gastrointestinal tract can be avoided. Difficulties in the acquisition of the images are no longer to be noted in the three-dimensional image reconstruction.

The second exemplary embodiment, depicted in FIG. 2, of the present invention relates to a wireless endoscope unit for non-invasive imaging in the region of the gastrointestinal tract of a patient, the endoscope unit being the size of a capsule 201 that can be swallowed by the patient. The endoscope unit includes an integrated miniature video camera 204 for recording (S1) a sequence of individual images, and an RF transmitter 205 for the wireless transmission (S2) of analog or digital image data in the form of ultrashort waves to the reception and evaluation device, which is located outside the body and includes the reception unit 103 or 108 and the host computer 106.

According to an embodiment of the invention, the capsule endoscope 200 has a permanent magnet 203 that is integrated in the capsule and, after the application of an external, spatially varying magnetic field $\vec{B}$, serves the purpose of moving the capsule-type endoscope unit 200 under active contactless control through the patient's gastrointestinal tract to be examined, independently of the external magnetic field.

FIG. 1 depicts a third exemplary embodiment of the present invention that relates to a medical apparatus 100 for recording and evaluating RF signals that are transmitted by the above-described capsule-type endoscope unit 200, and for the (pseudo-) three-dimensional representation of the images recorded by the capsule endoscope 200. The apparatus 100 can be used with particular advantage in the course of non-invasive gastroenterological endoscopy in the region of the human gastrointestinal tract.

The apparatus includes a reception unit 103 or 108, located outside the body, for receiving the image sequence transmitted by the capsule-type endoscope unit 200, for example in the form of ultrashort waves. The apparatus 100 also includes a computation unit 106 for decoding the image data transmitted by the capsule-type endoscope unit 200 and carrying out an image conditioning process for producing a three-dimensional representation of the surfaces displayed in the images.

A magnet tube 102 having field coils for generating a stationary homogeneous magnetic field $\vec{B}_0$, as well as one gradient coil each with an associated gradient amplifier 109 for the three Cartesian space coordinates x, y and z for locally changing the magnetic field in the ±x-, ±y- and/or ±z-directions, serve the purpose of exerting control in an active contactless fashion on a wireless endoscope unit 200, equipped with a permanent magnet 203, for example through the gastrointestinal tract of a patient. The apparatus 100 further includes an arrangement, distributed over the upper body of the patient, of metal sensors for locating metal parts of the capsule-type endoscope unit 200, and a measuring sensor with a transponder 105 as interface between the sensor arrangement 104 and the computation unit 106. A display device 107 connected to the computation unit 106 serves for visualizing the image data transmitted by the capsule-type endoscope unit 200 and conditioned by the computation unit 106.

Indicated according to an embodiment of the invention in this case is a three-sided view that is generated by the computation unit 106 by calculating virtual sectional views along sections parallel to the three orthogonal principal planes of the human body—"sagittal" (longitudinal section from front to rear), "coronal" (longitudinal section from left to right) and/or "transverse" or "axial" (cross section through the human body), and is displayed in three different control windows 107*a-c* of the display device 107. Moreover, the recorded image sequence can be played back in the form of a video film in real time or in fast forward mode in a fourth control window 107*d* of the display device 107.

According to a further exemplary embodiment of the present invention, the pseudo-three-dimensional representation, visualized via the display device 107, of the surroundings of the endoscope unit 200 can be inspected in the course of a virtual fly-through mode by varying the viewing perspective with the aid of control signals of an input unit (for example a computer mouse or a joystick).

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-assisted 3D imaging method for a wireless, capsule-type endoscope unit equipped with a video camera, comprising:
    recording images of surroundings of the endoscope unit;
    transmitting image data of the recorded images, in a wireless fashion, from the endoscope unit to at least one of a reception device and evaluation device;
    executing a pattern recognition algorithm for identifying substantially corresponding features of successive individual images of a recorded image sequence;
    carrying out an image processing procedure for the concatenation of individual images by superimposing the identified, substantially corresponding image features in order thereby to produce a pseudo three-dimensional representation of the surroundings of the endoscope unit;
    calculating distance squares ($d_{ij}^2 := d^2(\underline{x}_{Mi}, \underline{x}_{Rj})$) between the image parameters, stored in the form of N-dimensional feature vectors ($\underline{x}_{Mi}$), of recorded individual images with the image parameters, stored in the form of N-dimensional reference vectors ($\underline{x}_{Rj}$), of images of diseased tissue structures from a reference image database by calculating the square of the Euclidean length ($\|\Delta\underline{x}_{ij}\|_2$) of their difference vectors ($\Delta\underline{x}_{ij} := \underline{x}_{Mi} \underline{x}_{Rj}$); and
    determining the reference vectors ($\underline{x}_{Rj}$) of the reference images whose distance squares ($d_{ij}^2$) are a minimum in relation to the respective feature vectors ($\underline{x}_{Mi}$) of the individual images to be examined.

2. The computer-assisted 3D imaging method as claimed in claim 1, wherein, with each i-th recording, the position of the endoscope unit is detected and transmitted together with the image data to the reception and evaluation device and is digitally stored therein, i being a whole number greater than or equal to one.

3. The computer-assisted 3D imaging method as claimed in claim 2, wherein at least one of the position and orientation of the capsule-type endoscope unit is detected and inserted into the pseudo three-dimensional representation visualized via a display device.

4. The computer-assisted 3D imaging method as claimed in claim 2, wherein, for concatenation of two individual images (m, n), use is made of the path difference ($\Delta\underline{x}_{m,n} := \underline{x}_n - \underline{x}_m$), covered by the capsule-type endoscope unit and loaded with a weighting factor, between the instantaneous recording positions ($\underline{x}_m, \underline{x}_n$) of the unit for recording the two individual images (m, n).

5. The computer-assisted 3D imaging method as claimed in claim 4, wherein the instantaneous recording positions ($\underline{x}_m, \underline{x}_n$) of the capsule-type endoscope unit are determined by evaluating X-ray pictures in which the endoscope unit is identifiable.

6. The computer-assisted 3D imaging method as claimed in claim 4, wherein the instantaneous recording positions ($\underline{x}_m, \underline{x}_n$) of the capsule-type endoscope unit are determined by evaluating the signal transit times ($T_m, T_n$) of the wireless image data transmission from the endoscope unit to the reception device.

7. The computer-assisted 3D imaging method as claimed in claim 1, wherein at least one of the position and orientation of the capsule-type endoscope unit is detected and inserted into the pseudo three-dimensional representation visualized via a display device.

8. The computer-assisted 3D imaging method as claimed in claim 7, wherein the pseudo three-dimensional representation of the surroundings of the endoscope unit visualized via the display device, is inspectable in the course of a virtual endoscopy by varying the viewing perspective with the aid of control signals of an input unit.

9. The computer-assisted 3D imaging method as claimed in claim 1, wherein different camera perspectives of the surroundings of the endoscope unit are displayed by navigating a cursor in a control window of an operator interface, represented on a display device, of a computer program.

10. The computer-assisted 3D imaging method as claimed in claim 9, wherein the navigation is performed by way of input parameters.

11. The computer-assisted 3D imaging method as claimed in claim 9, wherein the navigation is performed by way of input parameters including magnitude of an advancing movement in a direction of movement of the capsule-type endoscope unit, and magnitude of rotary movement about an axis pointing in the direction of movement.

12. The computer-assisted 3D imaging method as claimed in claim 9, wherein the pseudo three-dimensional representation of the surroundings of the endoscope unit visualized via the display device, is inspectable in the course of a virtual endoscopy by varying the viewing perspective with the aid of control signals of an input unit.

13. The computer-assisted 3D imaging method as claimed in claim 1, wherein the pseudo three-dimensional representation of the surroundings of the endoscope unit visualized via a display device, is inspectable in the course of a virtual endoscopy by varying the viewing perspective with the aid of control signals of an input unit.

14. The computer-assisted 3D imaging method as claimed in claim 1, wherein, for concatenation of two individual images (m, n), use is made of the path difference ($\Delta \underline{x}_{m,n} := \underline{x}_n - \underline{x}_m$), covered by the capsule-type endoscope unit and loaded with a weighting factor, between the instantaneous recording positions ($\underline{x}_m, \underline{x}_n$) of the unit for recording the two individual images (m, n).

15. The computer-assisted 3D imaging method as claimed in claim 14, wherein instantaneous recording positions ($\underline{x}_m, \underline{x}_n$) of the capsule-type endoscope unit are determined by evaluating X-ray pictures in which the endoscope unit is identifyable.

16. The computer-assisted 3D imaging method as claimed in claim 14, wherein instantaneous recording positions ($\underline{x}_m, \underline{x}_n$) of the capsule-type endoscope unit are determined by evaluating the signal transit times ($T_m, T_n$) of the wireless image data transmission from the endoscope unit to the reception device.

17. The computer-assisted 3D imaging method as claimed in claim 1, wherein, for concatenation of two individual images (m, n), use is made of the path difference ($\Delta \underline{x}_{m,n} := \underline{x}_n - \underline{x}_m$), covered by the capsule-type endoscope unit and loaded with a weighting factor, between the instantaneous recording positions ($\underline{x}_m, \underline{x}_n$) of the unit for recording the two individual images (m, n).

18. A wireless endoscope unit in the form of a swallowable capsule, comprising
an integrated camera for recording a sequence of individual images;
a transmitter for wireless transmission of image data of the recorded images to a reception device and evaluation device; and
a permanent magnet, provided in the capsule, via which the endoscope unit is actively movable in a wireless fashion upon application of a temporally varying external magnetic field, wherein
with each i-th recording, the position of the endoscope unit is detected and transmitted together with the image data to the reception device and evaluation device and is digitally stored therein, i being a whole number greater than or equal to one, and
the evaluation device is configured to carry out an image processing procedure for concatenation of individual images, wherein the concatenation of two individual images (m, n), includes using the path difference ($\Delta \underline{x}_{m,n} := \underline{x}_n - \underline{x}_m$), covered by the capsule-type endoscope unit and loaded with a weighting factor, between the instantaneous recording positions ($\underline{x}_m, \underline{x}_n$) of the unit for recording the two individual images (m, n).

19. A medical apparatus for recording and evaluating signals from a capsule-type endoscope unit, comprising:
a reception unit for wireless reception of image information transmitted by the capsule-type endoscope unit;
a computation unit for decoding the image data transmitted by the capsule-type endoscope unit and for carrying out an image conditioning process for producing a pseudo three-dimensional representation of received image information; and
a display device for visualizing the conditioned image data, wherein
the computation unit is configured to calculate distance squares ($d_{ij}^2 := d^2(\underline{x}_{Mi}, \underline{x}_{Rj})$) between the image parameters, stored in the form of N-dimensional feature vectors ($\underline{x}_{Mi}$), of recorded individual images with the image parameters, stored in the form of N-dimensional reference vectors ($\underline{x}_{Rj}$), of images of diseased tissue structures from a reference image database by calculating the square of the Euclidean length ($\|\Delta \underline{x}_{ij}\|_2$) of their difference vectors ($\Delta \underline{x}_{ij} := \underline{x}_{Mi} \underline{x}_{Rj}$) and determine the reference vectors ($\underline{x}_{Rj}$) of the reference images whose distance squares ($d_{ij}^2$) are a minimum in relation to the respective feature vectors ($\underline{x}_{Mi}$) of the individual images to be examined.

20. The medical apparatus as claimed in claim 19, further comprising a magnet tube, including field coils for generating a stationary homogeneous magnetic field ($\vec{B}_0$), and one gradient coil, each with an associated gradient amplifier for three Cartesian space coordinates x, y and z for locally changing the magnetic field in the ±x-, ±y- and/or ±z-directions.

21. The medical apparatus as claimed in claim 20, further comprising:
a distributed arrangement of metal sensors for locating metal parts of the capsule-type endoscope unit; and
a measuring sensor, connected to the sensor arrangement, including a transponder as an interface between the sensor arrangement and the computation unit.

22. The medical apparatus as claimed in claim 19, further comprising:
a distributed arrangement of metal sensors for locating metal parts of the capsule-type endoscope unit; and
a measuring sensor, connected to the sensor arrangement, including a transponder as an interface between the sensor arrangement and the computation unit.

23. A 3D imaging method for a wireless, capsule-type endoscope unit equipped with a video camera, comprising:
identifying substantially corresponding features of successive individual images of a recorded sequence of images of surroundings of the endoscope unit;
concatenating individual images by superimposing identified, substantially corresponding image features in order thereby to produce a pseudo three-dimensional representation of the surroundings of the endoscope unit;
calculating distance squares ($d_{ij}^2 := d^2(\underline{x}_{Mi}, \underline{x}_{Rj})$) between the image parameters, stored in the form of N-dimensional feature vectors ($\underline{x}_{Mi}$), of recorded individual images with the image parameters, stored in the form of N-dimensional reference vectors ($\underline{x}_{Rj}$), of images of diseased tissue structures from a reference image database by calculating the square of the Euclidean length ($\|\Delta \underline{x}_{ij}\|_2$) of their difference vectors ($\Delta \underline{x}_{ij} := \underline{x}_{Mi} \underline{x}_{Rj}$); and
determining the reference vectors ($\underline{x}_{Rj}$) of the reference images whose distance squares ($d_{ij}^2$) are a minimum in relation to the respective feature vectors ($\underline{x}_{Mi}$) of the individual images to be examined.

24. The method of claim 23, wherein image data of the recorded images are transmitted, in a wireless fashion, from the endoscope unit to at least one of a reception device and evaluation device.

25. The method of claim 23, wherein a pattern recognition algorithm is executed to identify the substantially corresponding features of successive individual images.

26. A wireless endoscope unit in the form of a swallowable capsule, comprising
a video camera for recording a sequence of individual images;
a transmitter for wireless transmission of image data of the recorded images; and
a permanent magnet, provided in the capsule, via which the endoscope unit is actively movable in a wireless fashion upon application of a temporally varying external magnetic field, wherein
with each i-th recording, the position of the endoscope unit is detected and transmitted together with the image data to a reception and evaluation device and is digitally stored therein, i being a whole number greater than or equal to one, and
the evaluation device is configured to carry out an image processing procedure for concatenation of individual images, wherein the concatenation of two individual images (m, n), includes using the path difference ($\Delta x_{m,n} := x_n - x_m$), covered by the capsule-type endoscope unit and loaded with a weighting factor, between the instantaneous recording positions ($x_m$, $x_n$) of the unit for recording the two individual images (m, n).

27. A 3D imaging system for a wireless, capsule-type endoscope unit equipped with a video camera, comprising:
means for identifying substantially corresponding features of successive individual images of a recorded sequence of images of surroundings of the endoscope unit;
means for concatenating individual images by superimposing identified, substantially corresponding image features in order thereby to produce a pseudo three-dimensional representation of the surroundings of the endoscope unit;
means for calculating distance squares ($d_{ij}^2 := d^2(x_{Mi}, x_{Rj})$) between the image parameters, stored in the form of N-dimensional feature vectors ($x_{Mi}$), of recorded individual images with the image parameters, stored in the form of N-dimensional reference vectors ($x_{Rj}$), of images of diseased tissue structures from a reference image database by calculating the square of the Euclidean length ($\|\Delta x_{ij}\|_2$) of their difference vectors ($\Delta x_{ij} := x_{Mi} \, x_{Rj}$); and
means for determining the reference vectors ($x_{Rj}$) of the reference images whose distance squares ($d_{ij}^2$) are a minimum in relation to the respective feature vectors ($x_{Mi}$) of the individual images to be examined.

28. A medical apparatus for recording and evaluating signals from a capsule-type endoscope unit, comprising:
means for wireless reception of image information transmitted by the capsule-type endoscope unit;
means for carrying out an image conditioning process for producing a pseudo three-dimensional representation of the received image data;
means for calculating distance squares ($d_{ij}^2 := d^2(x_{Mi}, x_{Rj})$) between the image parameters, stored in the form of N-dimensional feature vectors ($x_{Mi}$), of recorded individual images with the image parameters, stored in the form of N-dimensional reference vectors ($x_{Rj}$), of images of diseased tissue structures from a reference image database by calculating the square of the Euclidean length ($\|\Delta x_{ij}\|_2$) of their difference vectors ($\Delta x_{ij} := x_{Mi} \, x_{Rj}$); and
means for determining the reference vectors ($x_{Rj}$) of the reference images whose distance squares ($d_{ij}^2$) are a minimum in relation to the respective feature vectors ($x_{Mi}$) of the individual images to be examined; and
means for displaying the conditioned image data.

29. A wireless endoscope unit in the form of a swallowable capsule, comprising
means for recording a sequence of individual images;
means for wireless transmission of image data of the recorded images; and
means, provided in the capsule, for actively moving the endoscope unit in a wireless fashion upon application of a temporally varying external magnetic field, wherein
with each i-th recording, the position of the endoscope unit is detected and transmitted together with the image data to a means for reception and evaluation and is digitally stored therein, i being a whole number greater than or equal to one, and
the means for reception and evaluation is for carrying out an image processing procedure for concatenation of individual images, wherein the concatenation of two individual images (m, n), includes using the path difference ($\Delta x_{m,n} := x_n - x_m$), covered by the capsule-type endoscope unit and loaded with a weighting factor, between the instantaneous recording positions ($x_m$, $x_n$) of the unit for recording the two individual images (m, n).

30. A computer-assisted 3D imaging method for a wireless, capsule-type endoscope unit equipped with a video camera, comprising:
recording images of surroundings of the endoscope unit;
transmitting image data of the recorded images, in a wireless fashion, from the endoscope unit to at least one of a reception device and evaluation device;
executing a pattern recognition algorithm for identifying substantially corresponding features of successive individual images of a recorded image sequence; and
carrying out an image processing procedure for the concatenation of individual images by superimposing the identified, substantially corresponding image features in order thereby to produce a pseudo three-dimensional representation of the surroundings of the endoscope unit, wherein
with each i-th recording, the position of the endoscope unit is detected and transmitted together with the image data to the reception and evaluation device and is digitally stored therein, being a whole number greater than or equal to one, and
for concatenation of two individual images (m, n), use is made of the path difference ($\Delta x_{m,n} := x_n - x_m$), covered by the capsule-type endoscope unit and loaded with a weighting factor, between the instantaneous recording positions ($x_m$, $x_n$) of the unit for recording the two individual images (m, n).

31. A computer-assisted 3D imaging method for a wireless, capsule-type endoscope unit equipped with a video camera, comprising:
recording images of surroundings of the endoscope unit;
transmitting image data of the recorded images, in a wireless fashion, from the endoscope unit to at least one of a reception device and evaluation device;
executing a pattern recognition algorithm for identifying substantially corresponding features of successive individual images of a recorded image sequence; and
carrying out an image processing procedure for the concatenation of individual images by superimposing the identified, substantially corresponding image features in order thereby to produce a pseudo three-dimensional representation of the surroundings of the endoscope unit, wherein for concatenation of two individual images (m, n), use is made of the path difference ($\Delta x_{m,n} := x_n - x_m$), covered by the capsule-type endoscope unit and loaded with a weighting factor, between the instantaneous recording positions ($x_m$, $x_n$) of the unit for recording the two individual images (m, n), and instantaneous recording positions ($x_m$, $x_n$) of the capsule-type endoscope unit are determined by evaluating X-ray pictures in which the endoscope unit is identifiable.

32. A computer-assisted 3D imaging method for a wireless, capsule-type endoscope unit equipped with a video camera, comprising:

recording images of surroundings of the endoscope unit;

transmitting image data of the recorded images, in a wireless fashion, from the endoscope unit to at least one of a reception device and evaluation device;

executing a pattern recognition algorithm for identifying substantially corresponding features of successive individual images of a recorded image sequence; and carrying out an image processing procedure for the concatenation of individual images by superimposing the identified, substantially corresponding image features in order thereby to produce a pseudo three-dimensional representation of the surroundings of the endoscope unit, wherein for concatenation of two individual images (m, n), use is made of the path difference ($\Delta x_{m,n} := x_n - x_m$), covered by the capsule-type endoscope unit and loaded with a weighting factor, between the instantaneous recording positions ($x_m$, $x_n$) of the unit for recording the two individual images (m, n), and instantaneous recording positions ($x_m$, $x_n$) of the capsule-type endoscope unit are determined by evaluating the signal transit times ($T_m$, $T_n$) of the wireless image data transmission from the endoscope unit to the reception device.

* * * * *